United States Patent
Black et al.

(10) Patent No.: US 9,557,283 B2
(45) Date of Patent: Jan. 31, 2017

(54) NANOCONFINEMENT PLATFORM FOR NANOSTRUCTURE QUANTIFICATION VIA GRAZING-TRANSMISSION X-RAY SCATTERING

(71) Applicant: Brookhaven Science Associates, LLC, Upton, NY (US)

(72) Inventors: Charles T. Black, New York, NY (US); Kevin G. Yager, Coram, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 14/713,081

(22) Filed: May 15, 2015

(65) Prior Publication Data
US 2015/0330920 A1    Nov. 19, 2015

Related U.S. Application Data

(60) Provisional application No. 61/993,353, filed on May 15, 2014.

(51) Int. Cl.
| G01N 23/00 | (2006.01) |
| G01N 23/20 | (2006.01) |
| G01N 23/201 | (2006.01) |

(52) U.S. Cl.
CPC ...... *G01N 23/20025* (2013.01); *G01N 23/201* (2013.01); *G01N 2223/054* (2013.01); *G01N 2223/309* (2013.01)

(58) Field of Classification Search
CPC ............ G01N 23/20025; G01N 23/201; G01N 2223/054; G01N 2223/309

(Continued)

(56) References Cited

U.S. PATENT DOCUMENTS 6,371,640 B1 *  4/2002  Hajduk ............... B01J 19/0046
                                            378/208
6,677,162 B1 *  1/2004  Wendelbo ........... B01J 19/0046
                                            222/168

(Continued)

OTHER PUBLICATIONS

Lu, X. et al., "Grazing-incidence transmission X-ray scattering: surface scattering in the Born approximation", J. Appl. Cryst. (2013) 46, pp. 165-172.

*Primary Examiner* — Michael Maskell
(74) *Attorney, Agent, or Firm* — Dorene M. Price

(57) ABSTRACT

A nano-confinement platform that may allow improved quantification of the structural order of nanometer-scale systems. Sample-holder 'chips' are designed for the GTSAXS experimental geometry. The platform involves fabricated nanostructured sample holders on and in one or more corners of a substrate support where the sample material of interest is positioned at the corner of the substrate support. In an embodiment, the substrate material making up the substrate support beneath the sample-holding area is removed. A scattering x-ray sample platform includes a substrate support arranged in a parallelepiped form, having a substantially flat base and a substantially flat top surface, the top surface being substantially parallel with the base, the parallelepiped having a plurality of corners. At least one corner of the substrate support has a sample holding area formed in the top surface of the substrate support and within a predetermined distance from the corner. The sample holding area includes a regular array of nano-wells formed in the top surface of the substrate support.

10 Claims, 3 Drawing Sheets

(58) Field of Classification Search
USPC .............................................. 378/86–90, 208
See application file for complete search history.

(56) References Cited

U.S. PATENT DOCUMENTS 6,806,093 B2 * 10/2004 Wendelbo ............ B01J 19/0046
222/168
7,597,852 B2 * 10/2009 Desrosiers ............ B01L 3/5085
250/428

* cited by examiner

NANOCONFINEMENT PLATFORM FOR NANOSTRUCTURE QUANTIFICATION VIA GRAZING-TRANSMISSION X-RAY SCATTERING

This application claims the benefit of U.S. Provisional Application No. 61/993,353, filed on May 15, 2014, the specification of which is incorporated by reference herein in its entirety for all purposes.

This invention was made with government support under contract number DE-AC02-98CH10886 and DE-SC0012704, awarded by the U.S. Department of Energy. The government has certain rights in the invention.

FIELD OF THE INVENTION

The instant disclosure is related to the field of x-ray scattering measurement, and more particularly to a substrate and method for use in grazing-incidence transmission small-angle X-ray scattering.

BACKGROUND

Quantification of the three-dimensional structure and order of nanometer-scale systems remains extremely challenging. Nanometer-scale microscopies, such as atomic force microscopy or scanning electron microscopy, arc typically used, but these may have difficulties probing through the depth of materials. Moreover, they generally cannot measure samples under realistic (in-situ) conditions. X-ray scattering is a well-known tool tor measuring structural order in-situ, with grazing-incidence small angle x-ray scattering (GISAXS) being used to probe thin films.

SUMMARY

In order to overcome drawbacks and disadvantages of quantifying data obtained by X-ray scattering in the present state of the art, provided according to the instant disclosure is a platform, comprising a substrate arranged in a parallel-epiped form, having a substantially flat base and a substantially flat top surface, the top surface being substantially parallel with the base, the parallelepiped having a plurality of corners. At least one corner of the substrate support has a sample holding area formed in the top surface of the substrate support and within a predetermined distance from the corner. The sample holding area includes an array of nano-wells formed in the top surface of the substrate.

The instant disclosure describes a nanoconfinement 'platform' that may allow for improved quantification of the structural order of nanometer-scale systems. Effectively, the platform may allow for 'images' of the organization of such systems to be obtained. The platform exploits established grazing incidence transmission x-ray scattering (GTSAXS) measurement geometry, but the present platform improves it in at least two ways: (1) sample-holder 'chips' on the platform may be designed for the GTSAXS experimental geometry; (2) These chips may have well-defined nano-wells, which may improve the x-ray scattering data or increase the availability of x-ray scattering data.

The platform may be fabricated on a substrate support to have nanostructered sample holders located in at least one corner, the sample-holding area, of the substrate support where a sample of interest may be positioned at the corner. This may allow the x-ray scattering signal to escape from the edge of the substrate (for measurement of undistorted and unattenuated scattering). Additionally, it may permit the sample to be rotated in-plane, which assists in providing for reconstruction of the complete three-dimensional scattering pattern.

In an embodiment of the present disclosure, the substrate support has substrate material beneath the sample-holding area that is removed. In an embodiment of the present disclosure, a recess may be formed in the substrate material beneath the sample holding area, the recess extending outward to open laterally from the platform. In an embodiment of the present disclosure, the sample holding area may be embodied in a shelf overlying the recess.

In an embodiment of the present disclosure, the sample holding area may be defined within a predetermined radius of the respective corner.

In an embodiment of the present disclosure, each of the plurality of corners comprises a sample holding area, with each sample holding area including a regular array of nano-wells formed in the top surface of the substrate. A recess may be provided in the substrate material beneath each sample holding area, extending outward to open laterally from the platform.

According to an embodiment of the present disclosure, the substrate material comprises water material having one or more of silicon, silicon dioxide, silicon nitride, aluminum oxide, titanium oxide or glass.

According to an embodiment of the present disclosure, the nano-wells are defined by an opening dimension of approximately 100 nm. Still further, the nano-wells may be defined by a depth dimension of approximately 100 nm. According to a more particular embodiment of the present disclosure, the nano-wells are spaced no less than approximately 200 nm between adjacent nano-wells.

BRIEF DESCRIPTION OF THE DRAWINGS

These and other purposes, goals and advantages of the present disclosure will become apparent from the following detailed description of example embodiments, read in connection with the accompanying drawings. Some embodiments are illustrated by way of example and not limitation in the figures of the accompanying drawings, in which like reference numerals refer to like structures across the several views.

DETAILED DESCRIPTION

A platform is disclosed herein that may be used as a variant technique of grazing-incidence scattering. The technique, known as grazing incidence transmission x-ray scattering (GTSAXS) allows scattered x-ray rays to escape from the edge of the substrate. This may improve the quality of data, allowing more complex structures to be solved.

Figure 1:
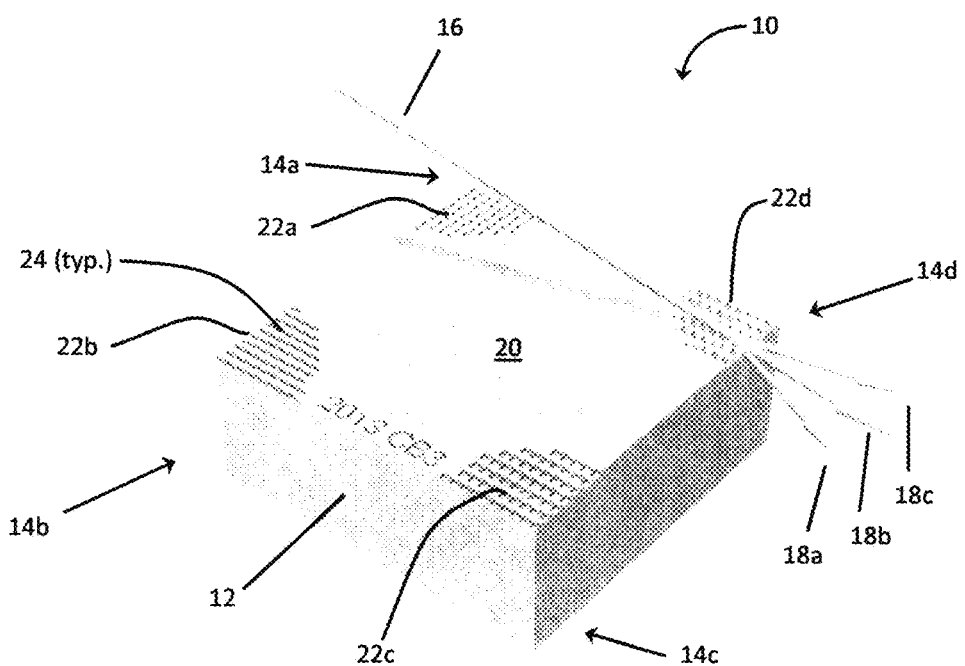
FIG. 1 illustrates a nano-confinement platform according to an embodiment of the present disclosure.

Referring now to FIG. 1, illustrated is a nano-confinement platform, generally 10, according to an embodiment of the present disclosure. The platform 10 comprises a substrate of material 12, e.g. and without limitation, crystalline or non-crystalline wafer material comprising silicon, silicon dioxide, silicon nitride, aluminum oxide, titanium oxide or glass, as will be known from the semiconductor arts. In particular, the crystalline silicon material lends itself to thin film processing techniques, as will be elaborated upon further hereinafter.

The substrate may also comprise a multi-component structure, for example a silicon dioxide ($SiO_2$) layer on top of a silicon layer. The present disclosure further contemplates a gold layer with the nano-wells on top of silicon. More specifically, the choice of substrate materials is known to influence the x-ray absorption length, and thereby allows one to control the measurement volume. Thus the material(s) used for the wells/substrate permit the investigator to either obtain large measurement areas, providing for example, good statistical sample. Alternately, a small measurement area provides the investigator the ability to conduct local probing. For example, aluminum and silicon, as well as their oxides, may be good materials for low-absorption of x-ray energy. Conversely, copper, tungsten, platinum, and gold may be good materials for high-absorption.

In order to minimize the opportunity for attenuation due to the substrate material 12, according to the present disclosure, the nano-structure sample is investigated at a corner 14a-d of the platform 10. In the exemplary embodiment, the platform is rectangular, particularly square, providing four corners 14a-d. Other shapes, e.g., triangular, pentagonal, hexagonal etc., may be used without departing from the scope of the present disclosure. Investigating the nano-structure sample particularly at a corner of the platform reduces the volume of substrate material 12 that is exposed to the grazing x-ray beam, represented in FIG. 1 by arrow 16. As a result attenuation of the scattered x-ray signal from the sample, represented by arrows 18a-c, is reduced. The corner may be slightly rounded. A corner 14a-d of the platform 10 is considered the area or vicinity of the platform 10 where two adjacent sides meet. Furthermore, any particular corner, e.g., 14a, will be considered to be bounded on any side only by an adjacent corner, i.e., 14b-d.

According to known GISAXS technique, for example, the nano-structure sample is applied to a platform in a thin film for investigation. However, according to the aforementioned disclosure of the GTSAXS technique, the nano-structure sample is examined at an edge of a sample holder on and in the platform, and more particularly at a corner thereof. Therefore, according to the instant disclosure, the platform 10 is provided on its uppermost surface 20, with sample holding areas 22a-d, which are preferably arranged within a predetermined distance of each corner 14a-d. Each sample-holding area 22a-d is provided with a plurality of nano-confinement wells (or bins), 24 (typ., See FIG. 2).

Figure 2:
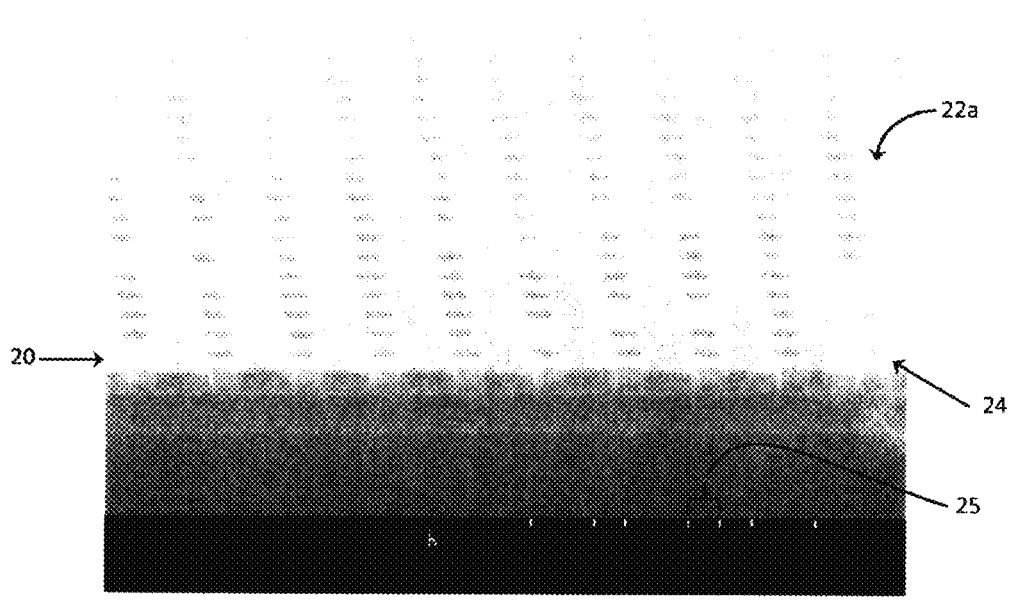
FIG. 2 illustrates a scanning electron micrograph of a sample holding area of the platform, including an arrayed plurality of nano-confinement wells.

Referring now to FIG. 2, illustrated is a scanning electron micrograph of a sample holding area 22a, including an arrayed plurality of nano-confinement wells 24 formed in the uppermost surface 20 of the platform 10. The nano-confinement wells 24 are arranged in a regular grid of volumes of the nano-structure sample in a defined pattern.

When the platform is exposed to the grazing x-ray beam 16, the interaction between the incident x-rays and the nano-structure material contained in the nano-confinement wells 24 establishes an interference pattern in the scattered x-ray transmission, which more clearly reveals the material characteristics of the nano-structure sample material under x-ray investigation. The scale of the exemplary embodiment of the platform 10 depicted in micrograph FIG. 2 is indicated by division 25, which is approximately 100 nm.

The arrangement of the nano-wells 24 in the sample holding area e.g., 22a, improve the known GTSAXS measurements in at least two ways. First, the precision of the size and regular spacing that is afforded by a lithographically defined grid of nano-wells 24 may cause an interference between the scattered x-rays from each of the nano-wells 24. Coherent interference between the x-rays scattered from sample material under investigation held in the plural nano-wells 24 may lead to improved scattering data quality, as a result of a number of sharp, well-defined, and bright peaks among the scattered x-rays observed on a detector. Resulting data exhibiting these improved characteristics may enable a more robust fitting of the x-ray scattering data. In particular, the well-defined peak heights can be used to extract the organization of material within the nano-wells.

Furthermore, the controlled size, shape, depth and surface chemistry of the nano-wells 24 may enforce a higher degree of order on the confined nano-structure material under investigation. This may also improve the quality of the x-ray scattering data. In particular, the defined volumes of the nano-structure finite-sized nano-objects under investigation can be located and oriented in the nano-wells 24 in fixed and defined positions and orientations. This registered and defined orientation and location of nano-structure material samples imposes a degree of order on that sample material that is not possible with a simple thin-film investigation as under GISAXS or even GTSAXS as previously practiced. While the nano-structure material under investigation may also be spread, in a thin-film manner, across a top surface of the platform, even if inadvertently by way of overflow, it remains that the x-ray signal scattered by the nano-structure material in the nano-wells 24 will be dominant over the scattered signal by any material in a thin film arrangement.

Consequently, it may be possible to extract enhanced information about the x-ray scattering signals and the structure of the nano-object. Accordingly, the array of nano-wells 24 may act as a synthetic lithographic crystalline structure applied to the nano-structure sample material under investigation. The results possible using the platform 10 according to the instant disclosure are analogous to x-ray scattering measurements as applied to naturally occurring crystals (e.g., protein crystals).

The illustrated scale in the micrograph, of FIG. 2 gives a sense of the scale of nano-confinement wells 24, in both diameter, depth and spacing. However, the precise dimensions of the nano-confinement wells 24 may be adjusted by those of ordinary skill in the art apprised of the instant disclosure without departing from its scope. The precise spacing and pattern of the array of nano-confinement wells 24 as compared with the characteristics of the grazing x-ray beam 16 will impact the results in at least two defined ways. Firstly, the spacing may influence the location of x-ray scattering peaks observed on the detector. The nano-well 24 spacing can be optimized for a particular x-ray scattering instrument, and measurements from multiple nano-well substrates of different spacing can be combined to yield higher-quality datasets. Secondly, the finite-size confinement of the nano-wells will influence the organization of materials. The size can be optimized to most efficiently organize different materials.

Accordingly, the platform 10 according to the instant disclosure lends itself to the study of the size and shape of nano-objects, nano-particle materials, finite sized nano-particle aggregates, proteins and protein complexes, viruses, or the like. Moreover, the presently disclosed platform 10 and methods are suitable for the investigation of bulk materials under confinement, including without limitation polymers, polymer blends, block copolymers, nano-composites, nano-particle packing, liquids, and other material types.

Figure 3:
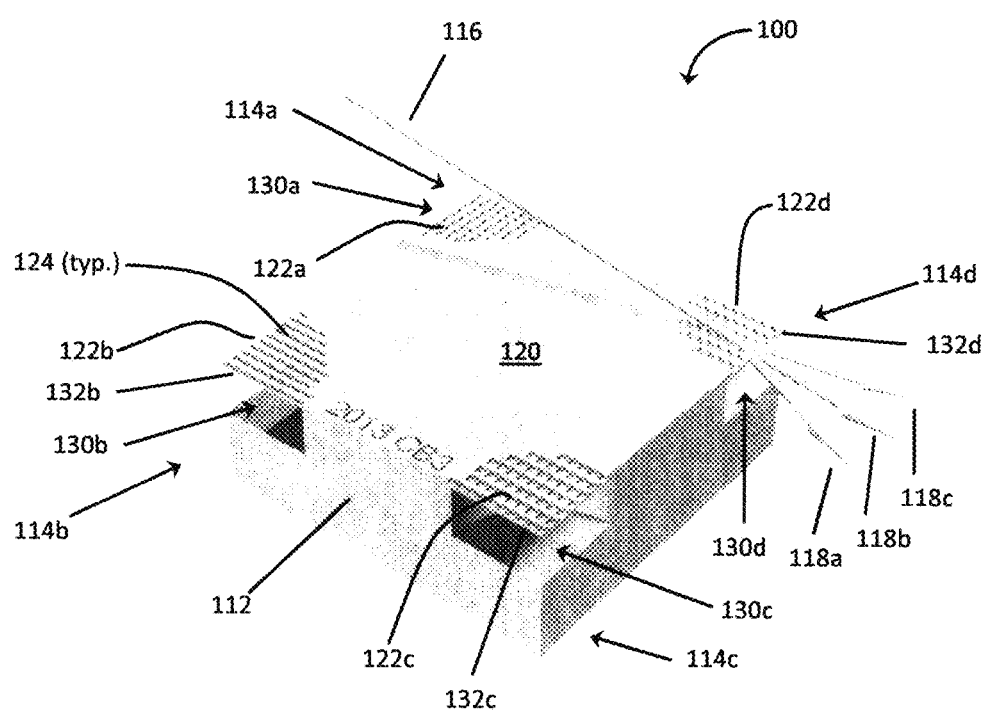
FIG. 3 illustrates a nano-confinement platform according to an embodiment of the present disclosure.

Furthermore, simulated measurements taken using the platform 100 in the embodiment of FIG. 3 suggests that the recess configuration may be particularly advantageous to leverage data quality improvements when using laboratory-scale x-ray beam instruments. For example, beam sources commonly available to many laboratories are lower energy, and lesser focused than, for example, than the National Synchrotron Light Source (NSLS) installation currently available at Brookhaven National Laboratory, or the NSLS-II. One difference between laboratory-scale instrumentation vs. a synchrotron is flux. For example, the flux of a lab-scale instrument may be on the order of between approximately $10^6$-$10^8$ photons/s. By comparison, synchrotron flux may be on the order of between $10^9$-$10^{14}$ photons/s. Laboratory-scale instrumentation will also vary from synchrotron instrumentation in other parameters, including such as for example energy, focus, divergence and resolution, however it will be appreciated by those skilled in the art that these additional parameters can vary even, within one category or the other, and it may be difficult in some instances to establish bright dividing lines between the categories with respect to these additional parameters.

For such highly focused incident x-ray beams, removing substrate material according to the embodiment platform 100 of FIG. 3 is believed to provide only marginal advantages. However, simulations have predicted comparative benefits in data quality when using the platform 100 of FIG. 3 in combination with the relative the lower power and poor focus characteristics of lesser laboratory-scale instruments.

Referring now to FIG. 3, illustrated is a nano-confinement platform, generally 100, according to an alternate embodiment of the present disclosure. Many features of the platform 100 will be apparent to those of ordinary skill by reference to the contemporaneous description of the earlier embodiment platform 10 in FIG. 1. Accordingly, a detailed description of all features of the second embodiment platform 100 will be dispensed with, except to highlight the salient differences between the two embodiments.

According to an embodiment, the platform 100 will have corners 114a-d. In the exemplary embodiment, the platform 100 is a four-sided polygon for example rectangular, or square in shape, providing four corners 114a-d that may be slightly rounded. Other shapes of the platform 100, e.g., triangular, pentagonal, hexagonal, etc., may be used without departing from the scope of the present disclosure.

A grazing x-ray beam is represented in FIG. 3 by arrow 116. The grazing-incidence x-ray beam is pointed at one of the edges of the substrate, with a controlled angle of incidence (on the order of 0.01 degrees to 2.0 degrees). The beam will typically be focused in the grazing-incidence direction (to a size ~200 micrometers to ~1 micrometer). Any x-ray beam energy is useable, though higher-energy x-ray beams (>10 keV) may suffer lower absorption loses.

The scattered x-ray signal from the sample is represented by arrows 118a-c. The platform 100 is provided on its uppermost surface 120 with sample holding areas 122a-d, which are preferably arranged within a predetermined distance of each corner 114a-d. Each sample-holding area 122a-d is provided with a plurality of nano-confinement wells, 124 (typ.).

Additionally, according to an embodiment of the platform 100, a recess 130a-d may be formed beneath each of the sample-holding areas 112a-d. Because of the recesses 130a-d, a shelf 132a-d is formed at the top surface 120 of the platform 100. The nano-confinement wells 124 are formed in the shelf 132a-d. In the exemplary embodiment, the lateral extent of the recesses 130a-d is roughly the same as that of the sample holding areas 122a-d. However, this is not strictly necessary, as the extent of the recesses can be greater or less, in accordance with the martial properties for the stability and integrity of the shelves 132a-d, and the attenuating properties of the substrate material 112, among other factors which will guide ordinarily skilled artisan having the benefit of Applicant's instant disclosure.

With reference to the platform 10 of FIG. 1, though also applicable to the platform 100 of FIG. 3, the following may be considered to be suitable exemplary physical dimensions. These descriptions and dimensions are offered with the understanding that they are not limiting on the scope of the present disclosure or invention. Considering the platform 10 of FIG. 1 as disclosed herein, it may be generally parallel-epiped in shape, in order that it may provide a stable base surface and top surface 20 substantially parallel with the base. The thickness of one exemplary embodiment may be approximately 500 μm in gross. The platform of the substrate 12 may be substantially rectangular, more specifically a square, providing four corners 12a-d. In the exemplary embodiment, each side has a dimension of approximately 15 mm. The sample holding areas 22a-d are formed on the top surface 20 within a distance of approximately 3 mm of their respective corner 14a-d.

Nano-wells 24 according to an exemplary embodiment may be formed on the order or between 10-300 nm, and in more particular cases approximately 100 nm, in diameter, whether round or prismatic, and have a similar scale of depth. Nano-wells 24 may be spaced from one another generally according to their size, but in certain embodiments on the order of 200-300 nm between adjacent ones. Specifically with regard to the embodiment of FIG. 3, the recesses 130a-d may be provided having a vertical dimension of approximately 150 μm. The periodicity of the ordered arrays of nano-wells 24 may also relate to the wavelength and strength or weakness of the x-ray beam. For example, spacing nano-wells 24 closer to one another provide results according to the presently disclosed methods in which the fundamental peaks of scatters x-ray energy may be more easily measured.

The shelf 132a-d may be provided at a thickness of approximately 5 μm, which compares with a nano-well 24, 124, depth and/or diameter on the order of approximately 0.1 μm. For example the thickness is desirably thin enough not to interfere with the x-ray beam but thick enough not to bend or warp. As noted earlier, the lateral extents of the recesses 130a-d are generally co-extensive with the extent of the sample holding areas 122a-d. The selection of a shape may correspond with a particular nano-object being studied and the way the particular nano-object packs in the nano-well.

Certain embodiments of the present disclosure have been described above in detail. However, it is desired to emphasize that this has been for the purpose of illustrating and describing the disclosure, and should not be considered as necessarily limitative of the disclosure, it being understood that many modifications can be made by those skilled in the art while still practicing the invention, which is defined solely according to the following claims. Variants of the above-disclosed and other matures and functions, or alternatives thereof, may be desirably combined into many other different systems or applications. Various presently unforeseen or unanticipated alternatives, modifications, variations, or improvements therein may be subsequently made by those skilled in the art in light of the instant disclosure, those also intended to be encompassed by the following claims.

The invention claimed is:

1. An x-ray scattering sample platform comprising:
   a substrate arranged in a parallelepiped form, having a substantially flat base and a substantially flat top surface, the top surface being substantially parallel with the base, the substrate having a plurality of corners;
   at least one of the corners of the substrate having a sample holding area formed in the top surface of the substrate and within a predetermined distance from the corner, the sample holding area comprising a regular array of nano-wells formed in the top surface of the substrate.

2. The platform according to claim 1, wherein the sample holding area is defined within a predetermined radius of the at least one corner.

3. The platform according to claim 1, further comprising a recess in the substrate beneath the sample holding area, extending outward to open laterally from the platform.

4. The platform according to claim 1, wherein the sample holding area is embodied in a shelf overlying a recess.

5. The platform according to claim 1, wherein each of the plurality of corners comprises a sample holding area, and each sample holding area includes a regular array of nano-wells formed in the top surface of the substrate.

6. The platform according to claim 5, further comprising a recess in the substrate beneath each sample holding area, extending outward to open laterally from the platform.

7. The platform according to claim 1, wherein the substrate comprises a wafer material, having one or more of silicon, silicon dioxide, silicon nitride, aluminum oxide, titanium oxide or glass.

8. The platform according to claim 1, wherein the nano-wells are defined by an opening dimension of at least approximately 10 nm.

9. The platform according to claim 1, wherein the nano-wells are defined by a depth dimension of at least approximately 10 nm.

10. The platform according to claim 1, wherein the nano-wells are spaced at least approximately 10 nm between adjacent nano-wells.

* * * * *